United States Patent [19]

Frankenreiter

[11] Patent Number: 4,926,873

[45] Date of Patent: May 22, 1990

[54] METHOD FOR MEASURING BLOOD PRESSURE AND APPARATUS FOR AUTOMATED BLOOD PRESSURE MEASURING

[75] Inventor: Michael Frankenreiter, Sindelfingen, Fed. Rep. of Germany

[73] Assignee: Hewlett-Packard Company, Palo Alto, Calif.

[21] Appl. No.: 325,627

[22] Filed: Mar. 20, 1989

[30] Foreign Application Priority Data

Aug. 1, 1988 [EP] European Pat. Off. ...... 88-112-448.1

[51] Int. Cl.$^5$ ............................................. A61B 5/02
[52] U.S. Cl. ................................... 128/681; 128/682; 128/683
[58] Field of Search .................. 128/672, 677–686

[56] References Cited

U.S. PATENT DOCUMENTS

| | | | |
|---|---|---|---|
| 4,349,034 | 9/1982 | Ramsey | 128/681 |
| 4,625,277 | 11/1986 | Pearce et al. | 128/682 X |
| 4,638,810 | 1/1987 | Ramsey, III et al. | 128/681 |
| 4,754,761 | 7/1988 | Ramsey, III et al. | 128/681 X |

FOREIGN PATENT DOCUMENTS

0208520 4/1986 European Pat. Off. .

Primary Examiner—Angela D. Sykes

[57] ABSTRACT

A method of non-invasive blood measuring is conducted according to the oscillometric method. The size of the decremental steps $\Delta p_{def}$ of a certain measuring cycle $C_{1+1}$ is a function of subject's actual blood pressure of the preceding measuring cycle $c_i$.

6 Claims, 2 Drawing Sheets

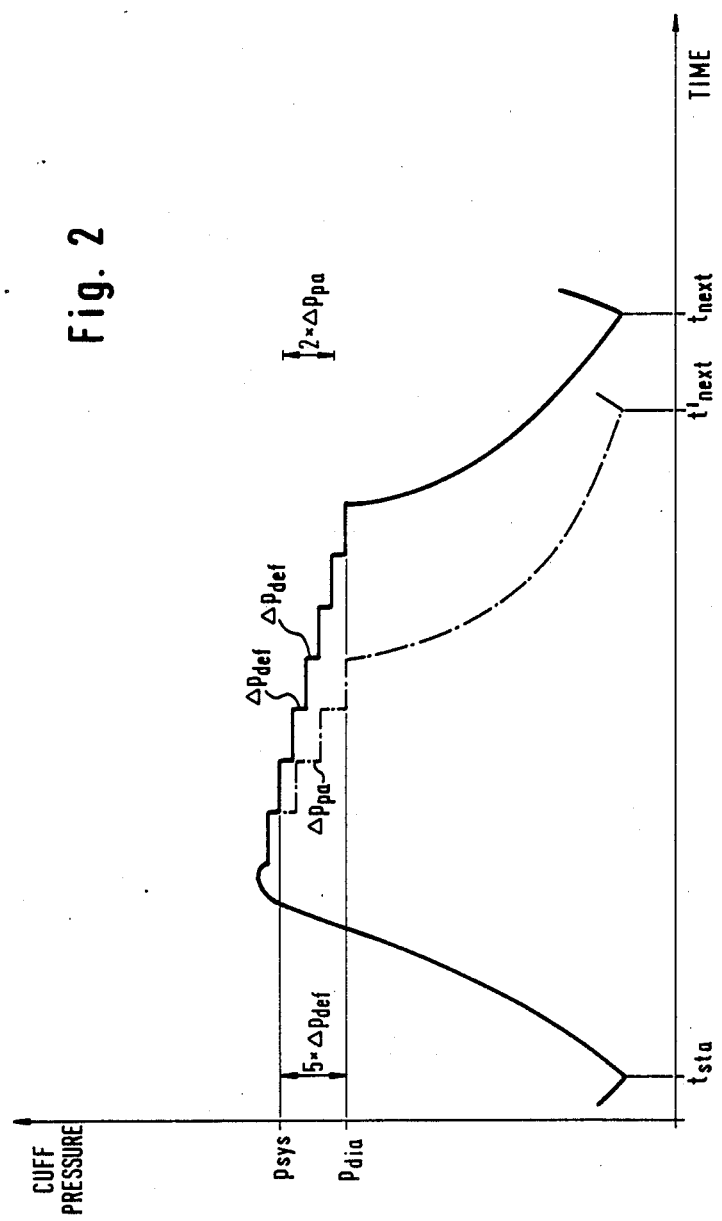

METHOD FOR MEASURING BLOOD PRESSURE AND APPARATUS FOR AUTOMATED BLOOD PRESSURE MEASURING

DESCRIPTION

The present invention relates to a method for measuring blood pressure, comprising the steps of applying a blood pressure cuff about a subject's limb containing an artery; inflating said cuff to a pressure $p_{max}$ above the systolic pressure $p_{sys}$, thereby occluding said artery, reducing cuff pressure from $p_{max}$ to at least a pressure $p_{min}$ below the diastolic pressure $p_{dia}$, thereby permitting an increasing flow through the progressively less occluded artery, reducing cuff pressure by definite steps $p_{def}$, detecting effects at the cuff caused by increasing flow through the progressively less occluded artery, processing these detected effects in processing means, displaying the said processed effects as subject's actual blood pressure values, and conducting a next subsequent blood pressure measuring cycle $c_{i+1}$ after a time interval.

The invention further relates to an apparatus for automated blood pressure measuring, in particular for cyclic measuring, the apparatus comprising an inflatable and deflatable pressure cuff that is applicable about a subject's limb containing an artery, means for inflating said cuff to a pressure $p_{max}$ above the systolic pressure $p_{sys}$, thereby occluding said artery, means for reducing cuff pressure from $p_{max}$ to at least a pressure $p_{min}$ below the diastolic pressure $p_{dia}$, thereby permitting an increasing flow through the progressively less occluded artery, said means for reducing allow a stepwise reduction of a cuff pressure, thereby stepwise deflating said cuff, means for detecting of effects at the cuff, caused by said increasing flow through said progressively less occluded artery, processing means for processing said detected effects and for converting said effects to subject's actual blood pressure values, and means for initiating a subsequent next measuring cycle $c_{i+1}$.

Such method and such an apparatus are known from EP-A2-0 208 520.

During such so-called "non-invasive" blood pressure measurements, an inflatable cuff is suitably located around a limb of a subject, for example a human, and is inflated up to a predetermined pressure $p_{max}$ above a systolic pressure $p_{sys}$, thereby occluding an artery. The limb may be an arm, in particular the upper arm, a foot, or a finger of a subject. Thereupon, cuff pressure is reduced with indefinite steps $\Delta p_{def}$. Such definite steps $\Delta p_{def}$ are, for example, on measuring a human adult 1.064 kPa (8 mmHg) or 0.532 kPa (4 mmHg) for neonates. During deflating of the, an increasing flow through the progressively less occluded artery is permitted. The effect at the cuff may be detected by the so-called "oscillometric method", for example as described within EP-A2-0 208 520.

The oscillometric method of measuring blood pressure is one of the most popular methods in commercially available systems. This method relies on measuring changes in arterial counterpressure, such as imposed by the inflatable cuff. At each pressure level after each cuff pressure reducing step, fluctuations are monitored. The resulting signals typically consist of the DC voltage with small superimposed variational components caused by the arterial blood pressure pulsations. After suitable filtering to reject the DC component and to provide amplification, peak pulse amplitudes above a given base line are measured and stored. As deflating of cuff continues, the peak oscillation amplitudes will normally increase from a lower level to a relative maximum, and thereafter will decrease. The lowest cuff pressure at which the oscillation amplitude has a maximum value is representative of mean arterial pressure. Systolic and diastolic pressures $p_{sys}$, $p_{dia}$ can be derived as a predetermined fraction of mean arterial pressure, or by more sophisticated methods of direct processing of the oscillatory complexes.

In some applications, several subsequent measurement cycles are necessary, for example in the so-called "automatic mode" or in the "stat mode", and become essential aspect of human and veterinary treatment. Such subsequent measurements are preferably conducted in emergency rooms, intensive and critical care units, and in the operation theatre.

One problem encountered in reducing cuff pressure with definite steps, for example with pressure decrements of 1.064 kPa (8 mm Hg), is that the number of steps depends on the difference between the systolic pressure $p_{dia}$ and the diastolic pressure $p_{sys}$ of the human individual.

A human adult may be characterized by his blood pressure values expressed in a pair of numbers representative to the systolic and diastolic pressures.

For example,

120/80, adult A, the so-called average human,
70/50, adult B, with hypotension,
110/40, adult C, for example a sportsman,
180/100, adult D, with hypertension.

The measuring of blood pressure of adult A needs seven steps, adult B only four steps, adult C eleven steps, and adult D twelve steps. The result of the adult B measurement based on only four steps is inaccurate and may deviate considerably from the actual values. The measurements of adults C and D are unnecessary long. The adult A measurements with about seven steps require only a short time interval, are most convenient for a human subject, and are sufficient for obtaining a good result with minimum deviation of the actual values. However, adults of kind A represent a minority among all humans, at which blood pressure measurements are usually conducted.

The method as described within EP-A2-0 208 520 uses non-uniform pressure decrementing steps for reducing the overall time for conducting a measurement cycle. The apparatus described within EP-A2-0 208 520 uses valves for deflating cuff having differently sized orifices. As long as the cuff pressure is relatively high, the deflation velocity through a smaller orifice valve is high. If cuff pressure has reduced to a particular pressure value, a second orifice is opened, thereby allowing a quicker deflation. As a result, a shorter overall measuring time is possible.

However, this method and apparatus depends on the structure of the cuff to be used and not on the subject to be measured. Therefore, the actual condition of subject to be measured, in particular, changes of condition during a measurement cycle in the so-called stat mode, are not taken into consideration. As a result, different number of deflating steps are performed, depending on the systolic and diastolic pressure of subject. As a result, measurements using only a few deflating steps are of less relevance than measurements with more deflating steps. However, use of numerous deflating steps may be unnecessary and may be disagreeable for subject to be measured.

It is, therefore, an object of the present invention to provide a method and an apparatus for measuring blood pressure as initially indicated allowing convenient measurements for subjects having different individuals blood pressure values.

This object is achieved by a method in which the size of the decremental steps $\Delta p_{def}$ of a certain measuring cycle $c_{i+1}$ is a function of subject's actual blood pressure of a preceding measuring cycle $c_i$. This object is further achieved by an apparatus having processing means, further comprising storing means for storing pressure values of subject within a cycle ci. The processing means provide means for reducing cuff pressure in decremental steps $\Delta p_{def}$ of cycle $c_{i+1}$ as a function of said stored pressure values of cycle $c_i$.

According to the invention, the size of the decremental steps $\Delta p_{def}$ in cycle $c_{i+1}$ is adapted to subject's actual blood pressure values of the preceding cycle $c_i$.

The pressure values of the preceding cycle $c_i$ indicate what kind of subject is to be measured, i.e. a subject with hypertension, normal blood pressure or hypotension. The size of deflating steps $\Delta p_{def}$ can now be adapted in such a manner that provides at the one side a convenient of deflating steps and provides at the other side a sufficient number of steps for obtaining measurement results with high relevance. Furthermore, if actual blood pressure values shift during a measurement cycle $c_i$ in the stat mode, for example based on a drug being applied to the subject, the deflating steps in cycle $c_{i+1}$ are adapted to such shifts, too. As a result, blood pressure measurings of high relevance are achieved, said measurings being agreeable to all different kinds of subjects to be measured.

According to another aspect of the invention, the size of decremental steps in cycle $c_{i+1}$ is $$\Delta p_{def} = \frac{p_{2ci} - p_{1ci}}{x} \qquad \text{Eq. I}$$

with $p_{2ci} \leq p_{max}$ in cycle $c_i$ $p_{1ci} \geq p_{min}$ in cycle $c_i$, $p_{2ci} > p_{1ci}$ and x=constant.

This has the advantage that the size of steps $\Delta p_{def}$ depends on two pressure values, being typical for the individual subject to be measured and being typical for the condition of the subject in the preceding measurement cycle $c_i$. The constant factor x leads to the same number of deflating steps $\Delta p_{def}$ during deflating cuff from pressure $p_{2ci}$ to pressure $p_{1ci}$. Therefore, each particular blood pressure value, for example the systolic pressure $p_{sys}$, of each cycle within a lot of cycles in the stat mode is of the same relevancy. Additionally, measuring a subject with hypertension or with hypotension, occur with the same number of incremental steps, at least within the interval $p_{2ci}-p_{1ci}$. As a result, measurements at different kinds of blood pressure type subjects give the same relevancy of values.

According to another aspect of the invention, $p_{2ci} = p_{sysci}$, $p_{1ci} = p_{diaci}$ and $3 \leq x \leq 6$.

This has the advantage that two particular pressure values are evaluated for determining the size of the incremental steps. The particular values $p_{sysci}$ and $p_{diaci}$ are essential ones for indicating the condition of subject in cycle $c_i$. Performing three six deflating steps between the systolic and diastolic pressure leads to agreeable measuring times per cycle using conventional oscillometric methods, in particular if measuring a human, and results in pressure values of high relevancy in view of the actual values.

According to another aspect of the invention, the size of decremental steps $\Delta p_{def}$ in a first cycle $c_0$ is adapted to a subject's known blood pressure data as the basis of decremental steps in cycle $c_0$.

This has the advantage that, in using the automatic mode, the first cycle $c_0$ is adapted to known blood pressure values obtained on earlier measurements. However, if no pressure values of subject are known, within the first cycle $c_0$ a predetermined size of incremental steps $\Delta p$ can be used.

According to another aspect of the invention, $\Delta p_{def}$ can vary within two limits $$\Delta p_{defmin} \leq \Delta p_{def} \leq \Delta p_{defmax}.$$

This has the advantage that in cases of measuring subjects having extremely individual pressure values, the size of decremental steps becomes neither too great nor too small.

According to another aspect of the invention, in particular if measuring a human, $\Delta p_{defmin}$ is about 0.5 kPa (4 mmHg), and $\Delta p_{defmax}$ is about 2 kPa (16 mmHg).

This has the advantage that the size of incremental pressure steps varies within limits being agreeable to any human, i.e. an adult or a neonate.

BRIEF DESCRIPTION OF THE DRAWINGS

Some embodiments of the present invention will now be described with reference to the accompanying drawings in which FIG. 2 shows a similar graph as FIG. 1, demonstrating a second embodiment according to the invention.

DESCRIPTION OF THE PREFERRED EMBODIMENTS

Figure 1:
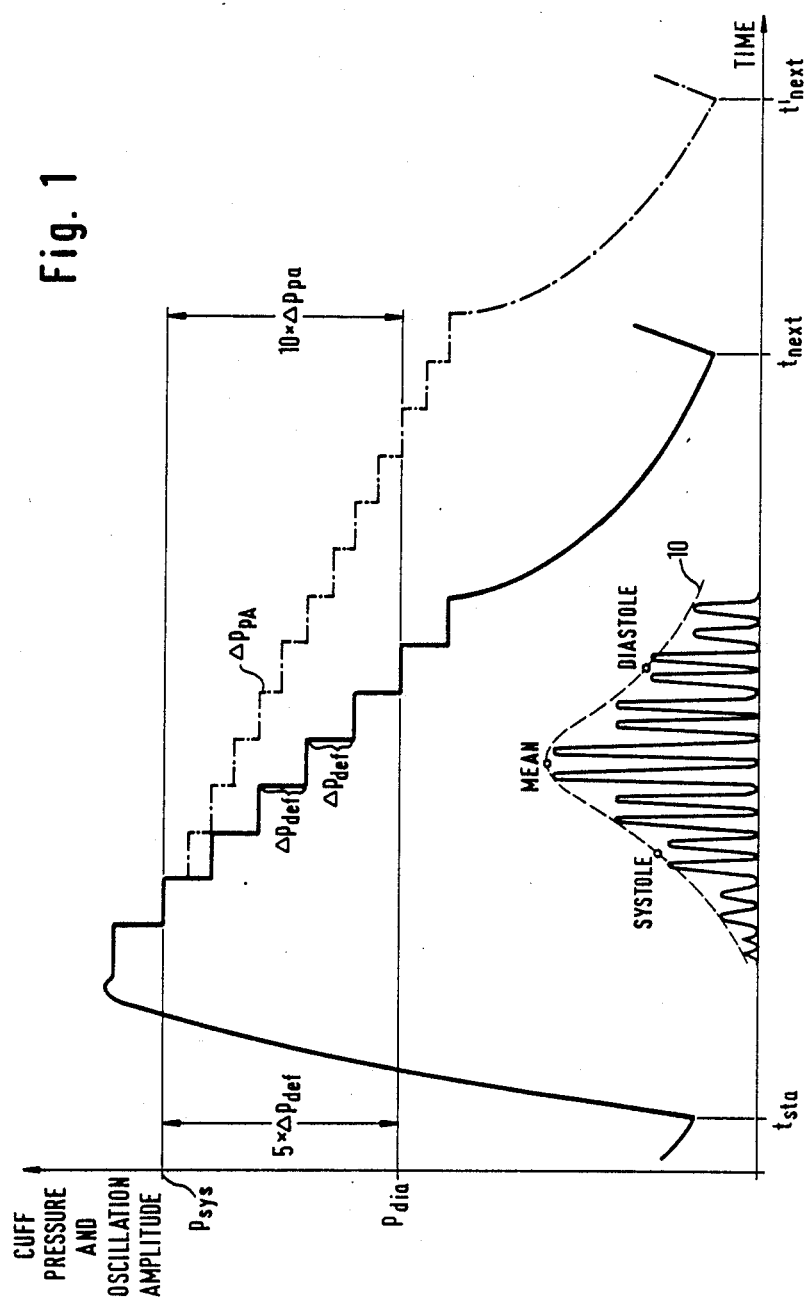
FIG. 1 shows a graph having plotted a cuff pressure via time, demonstrating a first embodiment according to the invention.

Referring now to FIG. 1, the graph shown is representative to a cuff pressure/time graph of a non-invasive blood pressure measurement. A blood pressure cuff is applied about a subject's artery and inflated above the systolic level $p_{sys}$, thus fully occluding the artery for a full heart cycle. The cuff pressure is thereafter reduced step by step to permit an increasing flow through the progressively less occluded artery (upper graph in FIG. 1 starting at time $t_{sta}$).

In accordance with conventional oscillometric techniques, pressure oscillations in the artery are sensed by changes in the counterpressure of the cuff, and, in turn, by a transducer. A measure of the peak amplitudes of the successively encountered oscillation complexes (not shown in the upper graph) are stored in a memory. Also retained is the cuff pressure obtained for each complex peak. As the measurement cycle proceeds, the peak amplitude of the blood pressure complexes generally become monitonically larger to a maximum and then become monitonically smaller as the cuff pressure continues toward deflation. The peak amplitude of the cuff pressure oscillation complexes and the corresponding occluding cuff pressure values are retained in a computer memory of the processing means.

The inflating of cuff occurs within two or four seconds, depending on cuff size and arrangement of cuff, e.g. about subject's upper arm or finger.

For interpretation of the peak amplitudes (within each step two amplitudes are measured), an envelope 10, surrounding the peak amplitudes, is determined (shown within FIG. 1 in the lower graph).

Within FIG. 1, the dash-dotted line demonstrates a conventional oscillometric method using predetermined sizes of incremental deflating steps $\Delta p_{pa}$. The size of steps $\Delta p_{pa}$ is 1.064 kPa (8 mmHg). The dash-dotted line is representative for an adult of type D with hypertension, with typical blood pressure values of 180/100. As a result, ten deflating steps $\Delta p_{pa}$ between $p_{sys}$ and $p_{dia}$ are necessary. As a result, the overall time of one measuring cycle starting from time $t_{sta}$ and ending on time $t'_{next}$ is unnecessary long.

According to the invention, using the formula in Eq. (I) with x=5, $$\Delta p_{def} = \frac{p_{2ci} - p_{1ci}}{5}$$

with
- $p_{2ci}$=180, representative to systolic pressure in the preceding cycle $c_i$, and
- $p_{1ci}$=100, representative to the diastolic pressure in cycle $c_i$, five steps of size $\Delta p_{def}$=16 (=16 mmHg=2.128 kPa) occur. Further deflating steps are performed above the systolic pressure and below the diastolic pressure. As a result, a shorter overall time for a measuring cycle starting at time $t_{sta}$ and ending on time $t_{next}$ is achieved. The resulting eight pairs of peak amplitudes are sufficient to determine the envelope 10, out of which envelope 10 the systole, mean and diastole pressure for the measuring cycle $c_{i+1}$ can be determined. Referring now to FIG. 2, a cuff pressure/time graph is shown, demonstrating a blood pressure measuring cycle $c_{i+1}$ of an adult B, having hypotension with typical values of 70/50.

A dash-dotted line demonstrates the result of a conventional oscillometric method using predetermined incremental steps $\Delta p_{pa}$=1.064 kPa (8 mmHg). As a result, only two deflating steps occur between the systolic pressure $p_{sys}$ and the diastolic pressure $p_{dia}$. An interpretation of the corresponding peak amplitudes or the envelope thereof is nearly impossible and leads to pressure values with considerable errors.

According to the invention, using the Eq. (II) with x=5, $$\Delta p_{def} = \frac{70 - 50}{5} = 4 \qquad (II)$$

with
- 70=$p_{2ci}$=$p_{sys}$,
- 50=$p_{ici}$=$p_{dia}$, the adult B is measured with the same number of deflating steps (i.e. 5) as adult D, as illustrated within FIG. 1.

As a result, the method according to the invention gives results of excellent and comparable relevancy.

The evaluation of subject's individual pressure values $p_{2ci}$ and $p_{ici}$ can be varied. Also, the constant X can vary, depending on the accuracy of the equipment used. For example, an equipment with sophisticated measuring means can use less deflating steps than used by simple equipment.

However, according to the teaching of the present invention, all measurements done with one choice of equipment leads to results being both adapted to the subject to be measured and being of same relevancy.

An apparatus according to the invention (not shown) comprises a cuff, inflating and deflating means, means for reducing cuff pressure and means for detecting of effects at the cuff as known in the art, for example as described within EP-A-0 208 520. The apparatus according to the invention further comprises processing means having storing means for storing pressure values $p_{2ci}$ and $p_{ici}$ of subject within a cycle $c_i$. Said processing means determines the difference between $p_{2ci}$ and $p_{ici}$ and subdivides said difference by a factor x, thereby determining the size of incremental pressure reducing step $p_{def}$ within cycle $c_{i+1}$. Said processing means provides said size values to the means for reducing cuff pressure, and said means reduce cuff pressure within cycle $c_{1+i}$ with said size values $\Delta p_{def}$.

Supervising means detect whether size value $\Delta p_{def}$ lies between upper and lower limits $\Delta p_{defmin}$ and $\Delta p_{defmax}$.

I claim:

1. A method for measuring blood pressure of a subject, the method comprising the steps of:
   (a) applying a blood pressure cuff about a subject's limb that contains an artery;
   (b) inflating the cuff to a pressure $p_{max}$ above the systolic pressure $p_{sys}$ of the subject, thereby occluding flow in the artery;
   (c) reducing cuff pressure from $p_{max}$ to a pressure $p_{min}$ below the diastolic pressure $p_{dia}$ of the subject in a sequence of cuff pressure abrupt decrements $\Delta p_{def}$ of approximately equal magnitude in a sequence of time intervals, where the pressure decrement for each time interval in cycle i+1 (i≧1) is determined by dividing the difference of two pressure values $p_{2ci}$ and $p_{1ci}$ by a positive constant that is independent of subject and that is no greater than six, where $p_{1ci}$ and $p_{2ci}$ are pressure values determined in cycle i that satisfy the relations $p_{min} \leq p_{1ci} < p_{2ci} \leq p_{max}$, thereby permitting sequentially increasing flow of blood through the artery;
   (d) determining the artery pressure within each time interval for which cuff pressure is approximately constant and determining $p_{sys}$, $p_{dia}$ and the mean arterial pressure for the cycle i+1;
   (e) displaying the blood pressure values $p_{sys}$ and $p_{dia}$ for the subject for the cycle i+1; and
   (f) repeating the preceding method steps (b), (c) and (d) at least once.

2. The method of claim 1, further comprising the steps of:
   choosing $p_{2ci}$ as $p_{sys\ ci}$=systolic pressure determined in cycle i, and
   choosing $p_{1ci}$ as $p_{dia\ ci}$=diastolic pressure determined in cycle i.

3. The method of claim 1, further comprising the steps of:

providing previously-determined systolic and diastolic pressure values, denoted $p_{sys,0}$ and $p_{dia,0}$, for said subject so that, for said first cycle i=1 said pressure decrement $\Delta p_{def}$ is determined by $$\Delta p_{def}^{(1)} = \frac{p_{sys,0} - p_{dia,0}}{x}.$$

4. Apparatus for measuring blood pressure of a subject, the apparatus comprising:
   an inflatable and deflatable pressure cuff that can be applied about a subject's limb containing an artery;
   pressure means for inflating the cuff to a pressure $p_{max}$ above the systolic pressure $p_{sys}$ of the subject;
   pressure reduction means for reducing the cuff pressure from $P_{max}$ to a pressure $p_{min}$ below the diastolic pressure $p_{min}$ of the subject in a sequence of cuff pressure abrupt decrements $\Delta p_{def}$ of approximately equal magnitude in a sequence of time intervals, where the pressure decrement for each time interval in cycle i+1 ($i \geq 1$) is determined by dividing the difference of two pressure values $p_{2ci}$ and $p_{1ci}$ by a positive constant that is independent of subject and that is no greater than six, where $p_{1ci}$ and $p_{2ci}$ are pressure values determined in cycle i that satisfy the relations $p_{min} \leq p_{1ci} < p_{2ci} \leq p_{max}$, thereby permitting sequentially increasing flow of blood through the artery;
   measurement means for determining the artery pressure within each time interval for which cuff pressure is approximately constant and for determining $p_{sys}$, $p_{dia}$ and the mean arterial pressure for the cycle i+1; and
   display means for displaying the blood pressure values $p_{sys}$ and $p_{dia}$ for the subject for cycle i+1.

5. The apparatus of claim 4, further comprising data input means for making available previously-determined systolic and diastolic pressure values, denoted $p_{sys,0}$ and $p_{dia,0}$, for said subject so that, for said first cycle i=1, said pressure decrement $\Delta p_{def}$ is determined by $$\Delta p_{def}^{(1)} = \frac{p_{sys,0} - p_{dia,0}}{x}.$$

6. The apparatus of claim 4, further comprising recycle means for causing said apparatus of claim 14 to perform two of said cycles i=1 and i=2 of blood pressure measurement.

* * * * *